United States Patent
Ragolia (10) Patent No.: US 10,408,838 B2
(45) Date of Patent: *Sep. 10, 2019

(54) NON-INVASIVE BIOMARKER TO IDENTIFY SUBJECT AT RISK OF PRETERM DELIVERY

(71) Applicant: NYU Winthrop Hospital, Mineola, NY (US)

(72) Inventor: Louis Ragolia, Mineola, NY (US)

(73) Assignee: NYU Winthrop Hospital, Mineola, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/708,582

(22) Filed: Sep. 19, 2017

(65) Prior Publication Data

US 2018/0003713 A1    Jan. 4, 2018

Related U.S. Application Data

(63) Continuation of application No. 14/438,110, filed as application No. PCT/US2013/066490 on Oct. 24, 2013, now Pat. No. 9,797,903.

(60) Provisional application No. 61/717,724, filed on Oct. 24, 2012.

(51) Int. Cl.
| | |
|---|---|
| *G01N 33/573* | (2006.01) |
| *A61K 31/5575* | (2006.01) |
| *A61K 31/195* | (2006.01) |
| *G01N 33/68* | (2006.01) |
| *A61K 45/06* | (2006.01) |
| *A61K 31/137* | (2006.01) |
| *A61K 31/454* | (2006.01) |
| *A61K 31/44* | (2006.01) |
| *A61K 31/4166* | (2006.01) |

(52) U.S. Cl.
CPC ......... *G01N 33/573* (2013.01); *A61K 31/137* (2013.01); *A61K 31/195* (2013.01); *A61K 31/4166* (2013.01); *A61K 31/44* (2013.01); *A61K 31/454* (2013.01); *A61K 31/5575* (2013.01); *A61K 45/06* (2013.01); *G01N 33/6893* (2013.01); *G01N 2333/99* (2013.01); *G01N 2800/368* (2013.01)

(58) Field of Classification Search
None
See application file for complete search history.

(56) References Cited

U.S. PATENT DOCUMENTS

| | | |
|---|---|---|
| 4,919,889 A | 4/1990 | Jones et al. |
| 5,096,830 A | 3/1992 | Senyei et al. |
| 5,223,440 A | 6/1993 | Teng et al. |
| 5,281,522 A | 1/1994 | Senyei et al. |
| 5,431,171 A | 7/1995 | Harrison et al. |
| 5,468,619 A | 11/1995 | Senyei et al. |
| 5,516,702 A | 5/1996 | Senyei et al. |
| 5,597,700 A | 1/1997 | Konstantinov et al. |
| 5,641,636 A | 6/1997 | Strauss, III et al. |
| 5,650,394 A | 7/1997 | Terao et al. |
| 5,698,404 A | 12/1997 | Strauss, III et al. |
| 5,783,396 A | 7/1998 | Voroteliak et al. |
| 5,877,029 A | 3/1999 | Fuks et al. |
| 5,891,722 A | 4/1999 | Fuks et al. |
| 5,968,758 A | 10/1999 | Fuks et al. |
| 6,126,597 A | 10/2000 | Smith et al. |
| 6,126,616 A | 10/2000 | Sanyal |
| 6,140,099 A | 10/2000 | Strauss, III |
| 6,149,590 A | 11/2000 | Smith et al. |
| 6,267,722 B1 | 7/2001 | Anderson et al. |
| 6,312,393 B1 | 11/2001 | Abreu |
| 6,394,952 B1 | 5/2002 | Anderson et al. |
| 6,395,499 B1 | 5/2002 | Abramovitz et al. |
| 6,410,583 B1 | 6/2002 | Labelle et al. |
| 6,544,193 B2 | 4/2003 | Abreu |
| 6,556,977 B1 | 4/2003 | Lapointe et al. |
| 6,605,705 B1 * | 8/2003 | Oda ................ C07K 16/40 435/326 |
| 6,610,480 B1 | 8/2003 | Shimkets et al. |
| 6,678,669 B2 | 1/2004 | Lapointe et al. |
| 6,790,635 B1 | 9/2004 | Seiki et al. |
| 6,867,051 B1 | 3/2005 | Anderson et al. |
| 6,875,567 B1 | 4/2005 | Shimkets et al. |
| 6,878,522 B2 | 4/2005 | Li et al. |
| 6,884,593 B1 | 4/2005 | Hirai et al. |
| 6,936,476 B1 | 8/2005 | Anderson et al. |
| 7,041,063 B2 | 5/2006 | Abreu |
| 7,109,044 B1 | 9/2006 | Oda et al. |

(Continued)

FOREIGN PATENT DOCUMENTS

| | | |
|---|---|---|
| EP | 0 913 405 A1 | 5/1999 |
| EP | 2912458 A1 | 9/2015 |

(Continued)

OTHER PUBLICATIONS

Shiki et al. in J. Obstet. Gynaecol. Res. vol. 30, No. 1:65-70 (2004) (Year: 2004).*
Mestecky et al. in Manual for Collection and Processing of Mucosal Specimens, AVEG Mucosal Immunology Laboratory, University of Alabama at Birmingham (Feb. 1999) (Year: 1999).*
Helliwell et al. in The Journal of Clinical Endocrinology & Metabolism 91(2):597-606 (2006) (Year: 2006).*
Olson et al. in Frontiers in Bioscience 12, 1329-1343 (2007) (Year: 2007).*

(Continued)

*Primary Examiner* — Dennis Heyer
(74) *Attorney, Agent, or Firm* — Wilson Sonsini Goodrich & Rosati (57) ABSTRACT

Methods for diagnosis to allow prediction of the likelihood of preterm birth based upon the concentration of lipocalin-type prostaglandin D2 synthase (L-PGDS) in cervical vaginal secretions. In addition, specific prostaglandin D2 receptor antagonists may represent novel tocolytic therapeutics.

15 Claims, 5 Drawing Sheets

(56) References Cited

U.S. PATENT DOCUMENTS

| | | | |
|---|---|---|---|
| 7,144,913 B2 | 12/2006 | Wang et al. | |
| 7,191,068 B2 | 3/2007 | Rosenfeld et al. | |
| 7,217,725 B2 | 5/2007 | Krauss et al. | |
| 7,228,295 B2 | 6/2007 | Lapointe et al. | |
| 7,270,970 B2 | 9/2007 | Anderson et al. | |
| 7,314,727 B2 | 1/2008 | Mase et al. | |
| 7,399,596 B2 * | 7/2008 | Oda | C12Q 1/533 435/7.1 |
| 7,403,805 B2 | 7/2008 | Abreu | |
| 7,488,585 B2 | 2/2009 | Meiri | |
| 7,517,889 B2 | 4/2009 | Harris et al. | |
| 7,524,636 B2 | 4/2009 | Bryant-Greenwood et al. | |
| 7,528,133 B1 | 5/2009 | Copland, III et al. | |
| 7,582,643 B2 | 9/2009 | Blake et al. | |
| 7,642,249 B2 | 1/2010 | Langevin et al. | |
| 7,654,957 B2 | 2/2010 | Abreu | |
| 7,709,272 B2 | 5/2010 | Fuks et al. | |
| 7,756,559 B2 | 7/2010 | Abreu | |
| 7,794,953 B2 | 9/2010 | Pentyala | |
| 7,809,417 B2 | 10/2010 | Abreu | |
| 7,811,279 B2 | 10/2010 | John | |
| 7,863,007 B2 | 1/2011 | Voroteliak | |
| 7,902,373 B2 | 3/2011 | Blake et al. | |
| 7,943,294 B2 | 5/2011 | Hussa et al. | |
| 8,060,195 B2 | 11/2011 | Gurewitsch et al. | |
| 8,067,445 B2 | 11/2011 | Hutchinson et al. | |
| 8,068,990 B2 | 11/2011 | Rosenfeld et al. | |
| 8,071,807 B2 | 12/2011 | Hutchinson et al. | |
| 8,114,610 B2 | 2/2012 | Fuks et al. | |
| 8,133,859 B2 | 3/2012 | Kimura et al. | |
| 8,160,692 B2 | 4/2012 | Principe et al. | |
| 8,193,183 B2 | 6/2012 | Lim et al. | |
| 8,242,145 B2 | 8/2012 | Hutchinson et al. | |
| 8,338,484 B2 | 12/2012 | Hutchinson et al. | |
| 8,362,044 B2 | 1/2013 | Hutchinson et al. | |
| 8,366,640 B2 | 2/2013 | Bauer et al. | |
| 8,372,581 B2 | 2/2013 | Hussa et al. | |
| 8,378,107 B2 | 2/2013 | Hutchinson et al. | |
| 8,383,654 B2 | 2/2013 | Hutchinson et al. | |
| 8,426,449 B2 | 4/2013 | Hutchinson et al. | |
| 8,497,381 B2 | 7/2013 | Hutchinson et al. | |
| 8,501,688 B2 | 8/2013 | Kimura et al. | |
| 8,501,959 B2 | 8/2013 | Hutchinson et al. | |
| 8,517,960 B2 | 8/2013 | Bauer et al. | |
| 8,524,748 B2 | 9/2013 | Hutchinson et al. | |
| 8,552,364 B2 | 10/2013 | Graves et al. | |
| 2001/0023419 A1 | 9/2001 | Lapointe et al. | |
| 2001/0025140 A1 | 9/2001 | Torok et al. | |
| 2001/0053876 A1 | 12/2001 | Torok et al. | |
| 2002/0022218 A1 | 2/2002 | Li et al. | |
| 2002/0031513 A1 | 3/2002 | Leibovitz | |
| 2002/0046054 A1 | 4/2002 | Morand et al. | |
| 2002/0049389 A1 | 4/2002 | Abreu | |
| 2003/0004906 A1 | 1/2003 | Lapointe et al. | |
| 2003/0027854 A1 | 2/2003 | Arimura | |
| 2003/0099651 A1 | 5/2003 | Leibovitz | |
| 2003/0105731 A1 | 6/2003 | Lapointe et al. | |
| 2003/0113319 A1 | 6/2003 | Leibovitz | |
| 2003/0139687 A1 | 7/2003 | Abreu | |
| 2003/0190678 A1 | 10/2003 | Mase et al. | |
| 2004/0014063 A1 | 1/2004 | Batteux et al. | |
| 2004/0038314 A1 | 2/2004 | Oda et al. | |
| 2004/0039297 A1 | 2/2004 | Abreu | |
| 2004/0039298 A1 | 2/2004 | Abreu | |
| 2004/0078219 A1 | 4/2004 | Kaylor et al. | |
| 2004/0100376 A1 | 5/2004 | Lye et al. | |
| 2004/0162323 A1 | 8/2004 | Krauss et al. | |
| 2004/0180934 A1 | 9/2004 | Wang et al. | |
| 2004/0185509 A1 | 9/2004 | Gervais et al. | |
| 2004/0197834 A1 | 10/2004 | Gervais et al. | |
| 2004/0197930 A1 | 10/2004 | Rosenfeld et al. | |
| 2004/0241752 A1 | 12/2004 | Anderson et al. | |
| 2004/0266025 A1 | 12/2004 | Hickok et al. | |
| 2005/0101841 A9 | 5/2005 | Kaylor et al. | |
| 2005/0131287 A1 | 6/2005 | Kaylor et al. | |
| 2005/0163771 A1 | 7/2005 | Leibovitz | |
| 2005/0215609 A1 | 9/2005 | Yoshikawa et al. | |
| 2005/0260683 A1 | 11/2005 | Bryant-Greenwood et al. | |
| 2005/0277912 A1 | 12/2005 | John | |
| 2006/0008923 A1 | 1/2006 | Anderson et al. | |
| 2006/0014302 A1 | 1/2006 | Martinez et al. | |
| 2006/0024722 A1 | 2/2006 | Fischer-Colbrie et al. | |
| 2006/0024723 A1 | 2/2006 | Hussa et al. | |
| 2006/0024724 A1 | 2/2006 | Hussa et al. | |
| 2006/0024725 A1 | 2/2006 | Hussa et al. | |
| 2006/0024757 A1 | 2/2006 | Hussa et al. | |
| 2006/0040337 A1 | 2/2006 | Meiri | |
| 2006/0166242 A1 | 7/2006 | Pennell et al. | |
| 2006/0166295 A1 | 7/2006 | Woods et al. | |
| 2006/0204532 A1 | 9/2006 | John | |
| 2006/0240495 A1 | 10/2006 | Buhimschi et al. | |
| 2006/0240498 A1 | 10/2006 | Friedman et al. | |
| 2007/0003992 A1 | 1/2007 | Pentyala | |
| 2007/0016074 A1 | 1/2007 | Abreu | |
| 2007/0020609 A1 | 1/2007 | Oda et al. | |
| 2007/0054951 A1 | 3/2007 | Li et al. | |
| 2007/0128589 A1 | 6/2007 | Sanders et al. | |
| 2007/0142718 A1 | 6/2007 | Abreu | |
| 2007/0161125 A1 | 7/2007 | Rosenfeld et al. | |
| 2007/0196864 A1 | 8/2007 | Pentyala | |
| 2007/0244131 A1 | 10/2007 | Lim et al. | |
| 2007/0249686 A1 | 10/2007 | Bonnert et al. | |
| 2007/0265278 A1 | 11/2007 | Harris et al. | |
| 2007/0265291 A1 | 11/2007 | Harris et al. | |
| 2008/0009552 A1 | 1/2008 | Pennell et al. | |
| 2008/0090759 A1 | 4/2008 | Kokenyesi et al. | |
| 2008/0194600 A1 | 8/2008 | Langevin et al. | |
| 2008/0227113 A1 | 9/2008 | Pentyala | |
| 2008/0233597 A1 | 9/2008 | Shiina et al. | |
| 2008/0254479 A1 | 10/2008 | Kokenyesi et al. | |
| 2008/0261922 A1 | 10/2008 | Carley et al. | |
| 2008/0299594 A1 | 12/2008 | Rosenfeld et al. | |
| 2009/0036469 A1 | 2/2009 | Stefany et al. | |
| 2009/0036761 A1 | 2/2009 | Abreu | |
| 2009/0055099 A1 | 2/2009 | Rosenfeld et al. | |
| 2009/0058072 A1 | 3/2009 | Weber et al. | |
| 2009/0068692 A1 | 3/2009 | Voroteliak | |
| 2009/0081206 A1 | 3/2009 | Leibovitz | |
| 2009/0171234 A1 | 7/2009 | Gurewitsch et al. | |
| 2009/0176804 A1 | 7/2009 | Yang et al. | |
| 2009/0197959 A1 | 8/2009 | Hutchinson et al. | |
| 2009/0227036 A1 | 9/2009 | Meiri | |
| 2009/0299212 A1 | 12/2009 | Principe et al. | |
| 2010/0004331 A1 | 1/2010 | Hutchinson et al. | |
| 2010/0008911 A1 | 1/2010 | Streisand et al. | |
| 2010/0017143 A1 | 1/2010 | Nagalla et al. | |
| 2010/0029006 A1 | 2/2010 | Rosenblatt et al. | |
| 2010/0075990 A1 | 3/2010 | Endres et al. | |
| 2010/0081673 A1 | 4/2010 | Hutchinson et al. | |
| 2010/0093621 A1 | 4/2010 | Kimura et al. | |
| 2010/0113503 A1 | 5/2010 | Hutchinson et al. | |
| 2010/0130574 A1 | 5/2010 | Eggan et al. | |
| 2010/0145180 A1 | 6/2010 | Abreu | |
| 2010/0251394 A1 | 9/2010 | Dore | |
| 2010/0298368 A1 | 11/2010 | Stearns et al. | |
| 2010/0311190 A1 | 12/2010 | Fuks et al. | |
| 2010/0318025 A1 | 12/2010 | John | |
| 2010/0323911 A1 | 12/2010 | Devarajan et al. | |
| 2010/0330077 A1 | 12/2010 | Armer et al. | |
| 2011/0002866 A1 | 1/2011 | Lubit et al. | |
| 2011/0021573 A1 | 1/2011 | Hutchinson et al. | |
| 2011/0021599 A1 | 1/2011 | Cotsarelis et al. | |
| 2011/0028717 A1 | 2/2011 | Kugimiya et al. | |
| 2011/0028807 A1 | 2/2011 | Abreu | |
| 2011/0034558 A1 | 2/2011 | Brittain et al. | |
| 2011/0039852 A1 | 2/2011 | Hutchinson et al. | |
| 2011/0040161 A1 | 2/2011 | Abreu | |
| 2011/0060026 A1 | 3/2011 | Hynd et al. | |
| 2011/0065139 A1 | 3/2011 | Mullerad et al. | |
| 2011/0071175 A1 | 3/2011 | Hynd et al. | |
| 2011/0090048 A1 | 4/2011 | Li et al. | |
| 2011/0098302 A1 | 4/2011 | Hutchinson et al. | |
| 2011/0098352 A1 | 4/2011 | Hutchinson et al. | |
| 2011/0112134 A1 | 5/2011 | Hutchinson et al. | |

(56) References Cited

U.S. PATENT DOCUMENTS

| | | |
|---|---|---|
| 2011/0130453 A1 | 6/2011 | Hutchinson et al. |
| 2011/0144160 A1 | 6/2011 | Hutchinson et al. |
| 2011/0152338 A1 | 6/2011 | Hutchinson et al. |
| 2011/0159533 A1 | 6/2011 | Karkouche |
| 2011/0166070 A1 | 7/2011 | Stewart |
| 2011/0184254 A1 | 7/2011 | Grove et al. |
| 2011/0190227 A1 | 8/2011 | Hutchinson et al. |
| 2011/0237972 A1 | 9/2011 | Garfield et al. |
| 2011/0245303 A1 | 10/2011 | Hutchinson et al. |
| 2011/0301168 A1 | 12/2011 | Hutchinson et al. |
| 2011/0312927 A1 | 12/2011 | Nachaegari et al. |
| 2011/0312928 A1 | 12/2011 | Nachaegari et al. |
| 2011/0312974 A1 | 12/2011 | Hutchinson et al. |
| 2011/0318308 A1 | 12/2011 | Ragolia |
| 2011/0319445 A1 | 12/2011 | Hutchinson et al. |
| 2012/0004233 A1 | 1/2012 | Stearns et al. |
| 2012/0009609 A1 | 1/2012 | Fuks et al. |
| 2012/0016029 A1 | 1/2012 | Hutchinson et al. |
| 2012/0022119 A1 | 1/2012 | Hutchinson et al. |
| 2012/0040356 A1 | 2/2012 | Hussa et al. |
| 2012/0046261 A1 | 2/2012 | Manuck et al. |
| 2012/0052595 A1 | 3/2012 | Wallace et al. |
| 2012/0058123 A1 | 3/2012 | Hutchinson et al. |
| 2012/0059055 A1 | 3/2012 | Hutchinson et al. |
| 2012/0082598 A1 | 4/2012 | Baydoun |
| 2012/0157422 A1 | 6/2012 | Poston et al. |
| 2012/0196285 A1 | 8/2012 | Okamoto et al. |
| 2012/0202740 A1 | 8/2012 | Kimura et al. |
| 2012/0238469 A1 | 9/2012 | Equils et al. |
| 2012/0238894 A1 | 9/2012 | Principe et al. |
| 2012/0270747 A1 | 10/2012 | Elovitz |
| 2013/0005728 A1 | 1/2013 | Harris et al. |
| 2013/0005741 A1 | 1/2013 | Harris et al. |
| 2013/0029957 A1 | 1/2013 | Giliyar et al. |
| 2013/0053670 A1 | 2/2013 | Aina-Mumuney et al. |
| 2013/0065902 A1 | 3/2013 | Aissaoui et al. |
| 2013/0071865 A1 | 3/2013 | Fuks et al. |
| 2013/0079375 A1 | 3/2013 | Endres et al. |
| 2013/0109685 A1 | 5/2013 | Aissaoui et al. |
| 2013/0158036 A1 | 6/2013 | Hutchinson et al. |
| 2013/0171672 A1 | 7/2013 | Hussa et al. |
| 2013/0177485 A1 | 7/2013 | Mullerad et al. |
| 2013/0225922 A1 | 8/2013 | Schentag et al. |

FOREIGN PATENT DOCUMENTS

| | | |
|---|---|---|
| WO | 93/09432 A1 | 5/1993 |
| WO | 93/09438 A1 | 5/1993 |

OTHER PUBLICATIONS

Shiki et al. in J. Obstet. Gynaecol. Res. vol. 30, No. 1 :65-70 (2004).
Gravett et al. in J Proteome Res. 6(1 ):89-96 (2007).
Helliwell et al. in The Journal of Clinical Endocrinology & Metabolism 91 (2):597-606 (2006).
Olson et al. in Frontiers in Bioscience 12, 1329-1343 (2007).
Mestecky et al. in Manual for Collection and Processing of Mucosal Specimens, AVEG Mucosal Immunology Laboratory, University of Alabama at Birmingham (Feb. 1999).
Pettipher et al. in Nature ReviewslDrug Discovery 6,313-325 (2007).
Caritis et al. in American Journal of Obstetrics and Gynecology 150(1),7-14 (1984) (Abstract).
Zegels et al. in Proteome Science 2009, 7:17.
Communication European Search Report dated Jun. 18, 2018 in connection with European Patent Application No. 18167167.8.
Lee et al., Journal of Maternal-Fetal and Neonatal Medicine, vol. 21, No. 2, Jan. 1, 2008, 89-94.
Rachel J. A. Helliwell, Jeffrey A. Keelan, Keith W. Marvin, Linda Adams, Maxwell C. Chang, Ashmit Anand, Timothy A. Sato, Simon O'Carroll, Tinnakorn Chaiworapongsa, Roberto J. Romero, and Murray D. Mitchell, "Gestational Age-Dependent Up-Regulation of Prostaglandin D Synthase (PGDS) and Production of PGDS-Derived Antiinflammatory Prostaglandins in Human Placenta", The Journal of Clinical Endocrinology & Metabolism, vol. 91, Issue 2, pp. 597-606, (Nov. 15, 2005), DOI: http://dx.doi.org/10.1210/jc.2005-1982.
Sunil Kumar, Thomas Palaia, Christopher E. Hall, Louis Ragolia. (2015) Role of Lipocalin-type prostaglandin D2 synthase (L-PGDS) and its metabolite, prostaglandin D2, in preterm birth. Prostaglandins & Other Lipid Mediators Online publication date: May 1, 2015.
L. Sykes, D. A. MacIntyre, T. G. Teoh, P. R. Bennett. (2014) Anti-inflammatory prostaglandins for the prevention of preterm labour. Reproduction 148, R29-R40 Online publication date: Jun. 24, 2014.
Robert J Phillips, Michel A Fortier, Andrés López Bernal. (2014) Prostaglandin pathway gene expression in human placenta, amnion and choriodecidua is differentially affected by preterm and term labour and by uterine inflammation. BMC Pregnancy and Childbirth 14, 241 Online publication date: Jan. 1, 2014.
Lynne Sykes, David A. MacIntyre, Xiao J. Yap, Sathana Ponnampalam, Tiong Ghee Teoh, Phillip R. Bennett. (2012) Changes in the Th1:Th2 Cytokine Bias in Pregnancy and the Effects of the Anti-Inflammatory Cyclopentenone Prostaglandin 15-Deoxy-$\Delta$ 12,14-Prostaglandin J 2 . Mediators of Inflammation 2012, 1-12 Online publication date: Jan. 1, 2012.
Sara F Rinaldi, James L Hutchinson, Adriano G Rossi, Jane E Norman. (2011) Anti-inflammatory mediators as physiological and pharmacological regulators of parturition. Expert Review of Clinical Immunology 7, 675-696 Online publication date: Sep. 1, 2011.
Patton, Stephanie M., Yong Won Cho, Thomas W. Clardy, Richard P. Allen, Christopher J. Earley, and James R. Connor. "Proteomic analysis of the cerebrospinal fluid of patients with restless legs syndrome/Willis-Ekbom." (2013).
Grisha Pirianov, Simon N. Waddington, Tamsin M. Lindström, Vasiliki Terzidou, Huseyin Mehmet, Phillip R. Bennett. (2013) The Cyclopentenone 15-Deoxy-$\Delta$12,14-Prostaglandin J2 Delays Lipopolysaccharide-Induced Preterm Delivery and Reduces Mortality in the Newborn Mouse. Endocrinology 150:2, 699-706 Online publication date: Feb. 1, 2009.
Khan, Abdul H., Ray J. Carson, and Scott M. Nelson. "Prostaglandins in labor—a translational approach." Front Biosci 13 (2008): 5794-5809.
Shiki, Yasuhiko, et al. "Changes of lipocalin—type prostaglandin D synthase level during pregnancy." Journal of Obstetrics and Gynaecology Research 30.1 (2004): 65-70, XP002903436, ISSN: 1341-S076, 001: 10.1111/J.1341-S076.2004.0015S.X.
Phillips, R. J., et al. "Genes for prostaglandin synthesis, transport and inactivation are differentially expressed in human uterine tissues, and the prostaglandin F synthase AKR1B1 is induced in myometrial cells by inflammatory cytokines." Molecular human reproduction 17.1 (2011): 1-13.
Warner, Timothy D., and Jane A. Mitchell. "Cyclooxygenases: new forms, new inhibitors, and lessons from the clinic." The FASEB Journal 18.7 (2004): 790-804.
Pirianov, Grisha, et al. "Endocrinology. First published ahead of print Oct. 9, 2008 as doi: 10.1210/en.2008-1178." (2008).
Fortier, M. A., K. Krishnaswamy, G. Danyod, S. Boucher-Kovalik, and P. Chapdalaine. "A postgenomic integrated view of prostaglandins in reproduction: implications for other body systems." J Physiol Pharmacol 59, No. Suppl 1 (2008): 65-89.
Marceau, Geoffroy, Jean-Marc Lobaccaro, Loïc Blanchon, and Vincent Sapin. Role of nuclear receptors Peroxisome Proliferator-Activated Receptors (PPARs) and Liver X receptors (LXRs) in the human placental pathophysiology. INTECH Open Access Publisher, 2012.
Pinhal-Enfield, Grace, Nagaswami S. Vasan, and Samuel Joseph Leibovich. The Role of Macrophages in the Placenta. INTECH Open Access Publisher, 2012.
Dwivedi, Chandraprakash, Kunal Chandrakar, Sandip Prasad Tiwari, Trilochan Satapathy, and Amit Roy. "Systematic review of the role of prostaglandins." World J Pharm Pharm Sci 3, No. 2 (2013): 2249-69.
Written Opinion of the International Searching Authority for International Application No. PCT/US2013/066490 dated Jan. 14, 2014.

(56) References Cited

OTHER PUBLICATIONS

International Search Report dated Jan. 14, 2014 issued in corresponding International patent application No. PCT/US2013/066490.

* cited by examiner

NON-INVASIVE BIOMARKER TO IDENTIFY SUBJECT AT RISK OF PRETERM DELIVERY

CROSS-REFERENCE TO RELATED APPLICATIONS

This application is a continuation of and claims priority to U.S. patent application Ser. No. 14/438,110, entitled NON-INVASIVE BIOMARKER TO IDENTIFY SUBJECT AT RISK OF PRETERM DELIVERY and filed Apr. 23, 2015, which is a 371 national phase of International Application No. PCT/2013/066490, filed Oct. 24, 2013 which claims the benefit of U.S. Provisional Patent Application 61/717,724, filed Oct. 24, 2012, the contents of which are incorporated herein by reference in their entirety.

TECHNICAL FIELD

This invention relates generally to methods for diagnosis of increased risk for preterm delivery during pregnancy. The invention also relates to compositions and methods for applications of specific prostaglandin D2 receptor (DP1 and DP2) antagonists as novel tocolytic therapeutic agents. The invention relates to applications wherein women with a diagnosis of preterm labor or at significant risk for preterm delivery, based on medical history and/or other factors, might be tested. The invention also relates to applications wherein pregnant women generally may be tested at 28 weeks of pregnancy to assess the likelihood of preterm delivery.

BACKGROUND OF THE INVENTION

Preterm birth is a leading cause of neonatal morbidity and mortality, accounting for 35% of infant healthcare spending and 10% of all childcare spending in the United States. In addition, medical costs from birth to one year of age are 10-fold greater for babies born premature and/or at low-birth weight when compared to those for babies born full-term. The rate of preterm birth has steadily increased by 20% since 1990, with 12.5% of all U.S. births being preterm births. Thus, there is a clear and significant need to understand the biological and molecular mechanisms leading to preterm birth, as well as to improve a physician's ability to predict which women are at risk for preterm delivery.

There are approximately 500,000 preterm births per year in the United States, of which approximately 30-70% are associated with an underlying infectious process. Infection is a major risk factor for pre-term birth after the most consistently identified risks factors, which include: a history of preterm birth, current multi-fetal pregnancy, and some uterine and/or cervical abnormalities. The ability to identify high-risk pregnancies at an early stage will lead to a significant reduction in the incidence of preterm birth and most likely reduce the incidence of fetal demise, decrease the rate of cerebral palsy, and other neuro-developmental delays. By improving our ability to identify those at risk of preterm birth, we also provide for the development of new and more effective treatments for preterm labor.

There is little overlap between the current biomarkers of preterm birth, suggesting that these various biomarkers predict different pathways that lead to preterm birth, and suggesting that the creation of a highly predictive biomarker would be beneficial. Currently, there are a handful of biomarkers which attempt to predict preterm labor in advance in order to prevent preterm delivery. These biomarkers include fetal fibronectin, salivary estriol, decidual proteins, and endocrinelparacrine. Fetal fibronectin and salivary estriol have been examined in some detail, with fetal fibronectin now being made available commercially. The fetal fibronectin test is based on the detection of fetal fibronectin, a fetal-specific glycosylated form of fibronectin. The theory is that increased amounts of fetal fibronectin signal the disturbance of the junction of the fetal membranes and the placental deciduas and therefore predicts delivery. In symptomatic pregnant women, the test has only limited effectiveness (58% sensitivity) to predict preterm delivery before the completion of 37 weeks gestation. The main benefit of the present test is the ability to exclude the possibility of preterm delivery (85% specificity) and to avoid unnecessary interventions. Parturition is comprised of 5 events: (1) membrane rupture; (2) cervical dilation; (3) myometrial contaction; (4) placental separation; and (5) uterine involution. While previously available tests might focus on detection of only a subset of these five events (and thus potentially lead to a heightened likelihood for "false positives" in the detection of a purported increased likelihood of preterm birth conditions), the present invention relates to a novel method for heightened sensitivity (e.g., detection of a unified factor relating to all 5 significant steps in parturition), coupled with a more practical effectiveness to diagnosis and possibly treat or prevent a broader range of potential preterm birth conditions. See, U.S. Pat. Nos. 4,919,889; 5,096,830; 5,223,440; 5,281,522; 5,431,171; 5,468,619; 5,516,702; 5,597,700; 5,641,636; 5,650,394; 5,698,404; 5,783,396; 5,877,029; 5,891,722; 5,968,758; 6,126,597; 6,126,616; 6,140,099; 6,149,590; 6,267,722; 6,312,393; 6,394,952; 6,544,193; 6,556,977; 6,610,480; 6,678,669; 6,867,051; 6,875,567; 6,936,476; 7,041,063; 7,191,068; 7,228,295; 7,270,970; 7,403,805; 7,488,585; 7,524,636; 7,528,133; 7,654,957; 7,709,272; 7,756,559; 7,809,417; 7,811,279; 7,863,007; 7,943,294; 8,060,195; 8,068,990; 8,114,610; 8,133,859; 8,160,692; 8,366,640; 8,372,581; 8,501,688; 8,517,960; 8,552,364; U.S. Pat. Pub. Nos. 20010023419; 20010025140; 20010053876; 20020031513; 20020046054; 20020049389; 20030004906; 20030099651; 20030105731; 20030113319; 20030139687; 20040014063; 20040039297; 20040039298; 20040078219; 20040100376; 20040197930; 20040241752; 20040266025; 20050101841; 20050131287; 20050163771; 20050260683; 20050277912; 20060008923; 20060014302; 20060024722; 20060024723; 20060024724; 20060024725; 20060024757; 20060040337; 20060166242; 20060166295; 20060204532; 20060240495; 20060240498; 20070016074; 20070128589; 20070142718; 20070161125; 20080009552; 20080090759; 20080254479; 20080299594; 20090036761; 20090055099; 20090058072; 20090068692; 20090081206; 20090171234; 20090227036; 20090299212; 20100008911; 20100017143; 20100029006; 20100093621; 20100145180; 20100311190; 20100318025; 20110028807; 20110040161; 20110065139; 20110090048; 20110159533; 20110166070; 20110184254; 20110237972; 20110312927; 20110312928; 20120009609; 20120040356; 20120046261; 20120052595; 20120082598; 20120157422; 20120196285; 20120202740; 20120238469; 20120238894; 20120270747; 20130029957; 20130053670; 20130071865; 20130171672; 20130177485; and 20130225922, each of which is expressly incorporated herein by reference.

Measurement of changes in Lipocalin-type prostaglandin D2 synthase (L-PGDS) levels in human cervicovaginal fluid has been suggested as a possible indicator of membrane rupture during pregnancy. Shiki Y, Shimoya K, Tokugawa Y, Kimura T, Koyama M, Azuma C, Murata Y, Eguchi N, Oda H, Urade Y 2004 Changes of lipocalin-type prostaglandin D synthase level during pregnancy. J Obstet Gynaecol Res 30:65-70 (37), each of which is expressly incorporated herein by reference.

Rachel J. A. Helliwell, Jeffrey A. Keelan, Keith W. Marvin, Linda Adams, Maxwell C. Chang, Ashmit Anand, Timothy A. Sato, Simon O'Carroll, Tinnakom Chaiworapongsa, Roberto J. Romero, and Murray D. Mitchell, "Gestational Age-Dependent Up-Regulation of Prostaglandin D Synthase (PGDS) and Production of PGDS-Derived Antiinflammatory Prostaglandins in Human Placenta", The Journal of Clinical Endocrinology & Metabolism, vol. 91 no. 2 pp. 597-606 (Feb. 1, 2006), each of which is expressly incorporated by reference, discuss that The two isoforms of PGDS (L-PGDS and H-PGDS) immunolocalized to distinct regions of human term and preterm gestational tissues. In placental villous tissues, specific labeling for L-PGDS was identified in the syncytiotrophoblast layer of both preterm and term placenta, with prominent staining of the apical membrane. At term, cytoplasmic syncytial staining was readily apparent in the syncytium, giving rise to a characteristic beaded appearance. Similarly, strong H-PGDS immunolabeling was observed in the syncytial layer of the preterm placenta. However, cellular localization of H-PGDS appeared to change with gestational age, and by term, immunoreactive H-PGDS was mainly localized to cells lining the villous capillaries, with little or no labeling observed in the syncytium. Labeling was completely absent in the corresponding negative controls in which primary antibody was preincubated with a 10-fold excess of blocking peptide or was omitted completely. In gestational membranes collected from both preterm and term pregnancies, strong immunolabeling for L-PGDS was observed in the cells of all tissues, including amnion epithelial, reticular, chorionic trophoblast, and decidual cells. In contrast, only very weak labeling of the gestational membranes was observed for H-PGDS. No labeling was observed in the corresponding negative controls. No significant staining of infiltrating leukocytes was apparent, although on some slides occasional cells positive for L- or H-PGDS were visualized among maternal blood cells. There was no statistical difference in the net amount of H-PGDS in any tissue as a result of the onset of labor at term or the presence of intrauterine infection preterm. Immunoreactive L-PGDS was undetectable in gestational tissues. L-PGDS mRNA was detectable in amnion, choriodecidual, and villous placental samples There was no significant effect of preterm intrauterine infection or term labor on the level of expression of L-PGDS mRNA. L-PGDS mRNA levels were significantly higher in the choriodecidua and placenta than in the amnion. There was no significant difference in the level of expression between the choriodecidua and placenta. The expression of H-PGDS mRNA was detectable in all three tissues, with no significant effect of preterm intrauterine infection or labor at term. Analyzing the combined data for each tissue revealed that the relative expression of H-PGDS mRNA was lowest in the amnion and choriodecidua, with a significantly higher level of expression in the villous placenta.

See also, Olson D M, Ammann C, "Role of the prostaglandins in labour and prostaglandin receptor inhibitors in the prevention of preterm labour", Front Biosci.; 12:1329-43 (Jan. 1, 2007), and Pirianov G, Waddington S N, Lindstrom T M, Terzidou V, Mehmet H, Bennett P R, "The cyclopentenone 15-deoxy-delta$^{12,14}$-prostaglandin J$_2$ delays lipopolysaccharide-induced preterm delivery and reduces mortality in the newborn mouse", Endocrinology 150(2):699-706 (Epub 2008 Oct. 9, February 20909), each of which is expressly incorporated herein by reference.

U.S. Pat. No. 7,399,596 and US 20070020609, expressly incorporated herein by reference, discusses using L-PGDS levels to predict pregnancy-induced hypertension. See also, U.S. Pat. Nos. 7,902,373, 7,794,953, 7,582,643, 7,314,727, 7,109,044, 6,790,635, 6,605,705, 6,410,583, 20110021599, 20100323911, 20100251394, 20080233597, 20080227113, 20070196864, 20070003992, 20040038314, 20030190678, each of which is expressly incorporated herein by reference.

Specific DP1/DP2 agonists and antagonists are available, e.g., BW245C (5-(6-carboxyhexyl)-1-(3-cyclohexyl-3-hydroxypropyl-hydantoin), AS702224, TS-022, 15R-methyl-PGD$_2$, 13-14-dihydro-15-keto-PGD$_2$, AM156, AM206, L-745870, 15R-PGD(2), MK-0524, BWA868C, BW24-SC, BAY-u3405, 15-deoxy-Delta12,14-prostaglandin J2 (15d-PGJ2), 11-deoxy-11-methylene PGD$_2$, G$_o$6983 (PKCα,Δ,ε, δ), G$_o$6976 (PKCα), GF10923X (PKCα,Δ,ε), LY333531 (PKC β), SB203580 (p38MAPK), SB203580, CD200, FGF18, GPRC5D, GPR49, LRRC15, Serpin A, CDT6, BMP2, LHX2, THBS1, MYCN, NR4A2, MEST, TM4SF1, CRLF1, TNFRSF12A, SELENBP1, GPR161, HEPH, FZD7, and CLIC4, CCL18, Col11A1, Col3A1, CD4, Cd1a, FCER1A, HLA-C, HLA-DPA1, IGF1, GPR105, PDGFRL, ADRA2A, CCL19, CORN, 16-phenoxy-17,18,19,20-tetranor PGD$_2$ N-cyclopropylamide, 16-phenoxy-17,18,19,20-tetranor PGD$_1$ N-cyclopropylmethylamide, 16-phenoxy-17, 18,19,20-PGD$_1$N-(1,3-dihydroxypropan-2-yl))amide; 17-phenyl-18,19,20-trinor PGD$_2$ N-cyclopropylamide, 17-phenyl-18,19,20-trinor PGD$_1$ N-cyclopropylmethylamide, 17-phenyl-18,19,20-trinor PGD$_2$N-(1,3-dihydroxypropan-2-yl))amide; 16-(3-chlorophenyl)-17,18,19,20-tetranor PGD$_2$ N-cyclopropylamide, 16-(3-chlorophenyl)-17,18,19, 20-tetranor PGD$_1$ N-cyclopropylmethylamide, 6-(3-chlorophenyl)-17,18,19,20-tetranor PGD$_1$ N-(1,3-dihydroxypropan-2-yl))amide, (Z)-isopropyl 7-((R)-2-((R)-3-hydroxy-5-phenylpentyl)-5-oxocyclopent-2-enyl)hept-5-enoate, (Z)-isopropyl 7-((R)-2-((R,E)-3-hydroxy-4-(3-(trifluoromethyl)phenoxy)but-1-enyl)-5-oxo-cyclopent-2-enyl)hept-5-enoate, (Z)—N-ethyl-7-((R)-2-((R,E)-3-hydroxy-4-(3-(trifluoromethyl)phenoxy)but-1-enyl)-5-oxocyclopent-2-enyl)hept-5-enamide, (Z)—N-ethyl-7-((R)-2-((S,E)-3-hydroxy-5-phenylpent-1-enyl)-5-oxocyclopen-t-2-enyl)hept-5-enamide, (Z)-7-((R)-2-((R,E)-3-hydroxy-4-(3-(trifluoromethyl)phenoxy)but-1-enyl)-5-oxocyclopent-2-enyl)hept-5-enoic acid, (Z)-7-((R)-2-((R,E)-3-hydroxy-4-(3-(trifluoromethyl)phenoxy)but-1-enyl)-5-oxocyclopent-2-enyl)-N-methylhept-5-enamide, (Z)-7-((R)-2-((R,E)-4-(3-chlorophenoxy)-3-hydroxybut-1-enyl)-5-oxocyclope-nt-2-enyl)hept-5-enoic acid, (Z)-isopropyl 7-((R)-2-((R,E)-4-(3-chlorophenoxy)-3-hydroxybut-1-enyl)-5-oxocyclopent-2-enyl)hept-5-enoate, (Z)-7-((R)-2-((R,E)-4-(3-chlorophenoxy)-3-hydroxybut-1-enyl)-5-oxocyclopent-2-enyl)-N-methylhept-5-enamide or a pharmaceutically acceptable salt, hydrate, solvate, prodrug or metabolite thereof. These agents may be used alone or in combination, and may be administered concurrently or sequentially. See also, 2011/0144160, 2011/0130453, 2011/0112134, 2011/0098352, 2011/0098302, 2011/0071175, 2011/0060026, 2011/0034558, 2011/0028717, 2011/0021599, 2011/0021573, 2011/0002866, 2010/0330077, each of which is expressly incorporated herein by reference.

SUMMARY OF THE INVENTION

This invention describes, for example, methods to apply and correlate the clinical measurement of L-PGDS concentrations of cervical vaginal secretions from pregnant women with the attendant likelihood of term or preterm delivery.

The invention also describes methods and compositions, specifically prostaglandin D2 (DP1 and DP2) receptor antagonists or inhibitors, as potential tocolytic agents.

It is therefore an object to provide a method for assessing the likelihood of preterm delivery for a pregnant woman, the method comprising collecting a cervical vaginal secretion sample from a pregnant woman; and measuring lipocalin-type prostaglandin D2 synthase (L-PGDS) concentration levels from the sample, wherein L-PGDS concentration levels correlate to and indicate an above or below average likelihood relative to the relevant standard population for preterm delivery.

According to one embodiment, an L-PGDS concentration level higher than 1.8 μg/ml indicates an increased likelihood for preterm delivery.

The method may advantageously be applied to a pregnant woman has intact amniotic membranes.

The cervical vaginal secretion may be collected with a sponge.

Based on the L-PGDS level, at least one prostaglandin D2 receptor antagonist may be administered as a tocolytic agent. The at least one prostaglandin D2 receptor antagonist may comprises a DP1 receptor antagonist and/or a DP2 receptor antagonist.

The L-PGDS concentration level may be determined using an antibody sandwich Enzyme-Linked ImmunoSorbent Assay (ELISA). The L-PGDS concentration levels may be normalized to protein levels in the cervical vaginal secretions for analysis.

Another object provides a method for treatment of preterm labor, comprising administration of a therapeutic amount of at least one prostaglandin DP1 or prostaglandin DP2 receptor antagonist to a pregnant woman such that preterm delivery is avoided or mitigated.

The administration may be selectively in dependence on a measured L-PGDS level, for example in a cervical vaginal secretion.

The at least one prostaglandin DP1 or prostaglandin DP2 receptor antagonist comprises one or more agents selected from the group consisting of AM156 ({2'-[(cyclopropan-ecarbonyl-ethyl-amino)-methyl]-6-methoxy-4'-trifluoro-methyl-biphenyl-3-yl}-acetic acid, sodium salt), and AM206 (5-{2-[(benzoyloxycarbonyl-ethyl-amino)-methyl]-4-trifluoromethyl-phenyl}-pyridin-3-yl)-acetic acid, sodium salt), MK-0524 ([(3R)-4-(4-Chloro-benzyl)-7-fluoro-5-(methylsulfonyl)-1,2,3,4-tetrahydrocyclopenta[b]indol-3-yl]-acetic Acid), AM-853 (2-(4-(4-(tert-butylcarbamoyl)-2-(2-chloro-4-cyclopropylphenyl sulfonamido)phenoxy)-5-chloro-2-fluorophenyl)acetic acid), BW868C (3-benzyl-5-(6-carbohexyl)-1-(2-cyclohexyl-2-hydroxyethylamino)-hydantoin), S-5751 ((Z)-7-[(1R,2R,3S,5S)-2-(5-hydroxy benzo[b]thiophen-3-ylcarbonylamino)-10-norpinan-3-yl] hept-5-enoic acid), and BAY-u3405 (Ramatroban, 3(R)-[[(4-fluorophenyl) sulphonyl]amino]-1,2,3,4-tetrahydro-9H-carbazole-9-propanoic acid).

Alternately, an L-PGDS inhibitor may be used, for example, AT-56 (4-dibenzo[a,d]cyclohepten-5-ylidene-1-[4-(2H-tetrazol-5-yl)-butyl]-piperidine).

Resveratrol has been shown to reduce formation of Prostaglandin D2 presumably by inhibiting cyclooxygenase (COX), especially COX-2. See, Lena Wendeburg, Antonio Carlos Pinheiro de Oliveira, Harsharan S Bhatia, Eduardo Candelario-Jalil and Bernd L Fiebich, "Resveratrol inhibits prostaglandin formation in IL-1β-stimulated SK-N-SH neuronal cells", J. Neuroinflammation 2009, 6:26, expressly incorporated herein by reference. Therefore, resveratrol or another non-teratogenic COX-2 inhibitor may advantageously be employed.

The at least one prostaglandin DP1 or prostaglandin DP2 receptor antagonist is administered orally, by inhalation, through a mucous membrane, transdermally, topically, rectally, or parenterally.

The at least one prostaglandin DP1 or prostaglandin DP2 receptor antagonist may be administered to achieve concurrent therapeutic effect with another tocolytic agent which is not a prostaglandin D2 receptor antagonist. For example, the other tocolytic agent may comprise a β2 agonist, such as terbutaline, Ritodrine, Fenoterol, or Salbutamol. The other tocolytic agent may also comprise a non-steroidal anti-inflammatory drug cyclooxygenase inhibitor, such as Indomethicin or sulindac. The tocolytic may be a calcium channel blocker, such as nifedipine, a myosin light chain inhibitor such as magnesium sulfate, or an axytocin inhibitor such as Atosiban.

A further object provides a pharmaceutical formulation comprising a therapeutic amount of a non-teratogenic comprising at least one prostaglandin DP1 or prostaglandin DP2 receptor antagonist and/or an L-PGDS inhibitor, in an effective amount to delay preterm delivery in a pregnant human when administered in repeated doses. The at least one prostaglandin DP1 or prostaglandin DP2 receptor antagonist may comprise, for example, one or more agents selected from the group consisting of AM156 ({2'-[(cyclopropan-ecarbonyl-ethyl-amino)-methyl]-6-methoxy-4'-trifluoro-methyl-biphenyl-3-yl}-acetic acid, sodium salt), and AM206 (5-{2-[(benzoyloxycarbonyl-ethyl-amino)-methyl]-4-trifluoromethyl-phenyl}-pyridin-3-yl)-acetic acid, sodium salt), MK-0524 ([(3R)-4-(4-Chloro-benzyl)-7-fluoro-5-(methylsulfonyl)-1,2,3,4-tetrahydrocyclopenta[b]indol-3-yl]-acetic Acid), AM-853 (2-(4-(4-(tert-butylcarbamoyl)-2-(2-chloro-4-cyclopropylphenyl sulfonamido)phenoxy)-5-chloro-2-fluorophenyl)acetic acid), BW868C (3-benzyl-5-(6-carbohexyl)-1-(2-cyclohexyl-2-hydroxyethylamino)-hydantoin), S-5751 ((Z)-7-[(1R,2R,3S,5S)-2-(5-hydroxy benzo[b]thiophen-3-ylcarbonylamino)-10-norpinan-3-yl] hept-5-enoic acid), and BAY-u3405 (Ramatroban, 3(R)-[[(4-fluorophenyl) sulphonyl]amino]-1,2,3,4-tetrahydro-9H-carbazole-9-propanoic acid), and the L-PGDS inhibitor may comprise AT-56 (4-dibenzo[a,d]cyclohepten-5-ylidene-1-[4-(2H-tetrazol-5-yl)-butyl]-piperidine).

DETAILED DESCRIPTION

Methods and Procedures for Risk Assessment for Preterm Delivery.

Cervical vaginal secretions (CVS) are readily collected and constitute a minimally invasive procedure. During a sterile speculum examination of a pregnant woman, a Weekgel sponge is applied into the cervical os for approximately one minute. The sponge is then removed and placed in a buffer solution containing physiological saline, Trizma buffer, protease inhibitors (EDTA, phenylmethylsulfonyl fluoride, pepstatin) and antibacterial agents (such as sodium azide). This sample collection process is very similar to that used for other routine clinical assays (e.g., fetal fibronectin) that use cervical secretions for the starting sample material. Preferably, the buffer solution has a low protein concentration, e.g., is produced with a small amount or no bovine serum albumin (BSA). This BSA is not required to stabilize the L-PGDS, and may interfere with its measurement.

L-PGDS concentration levels from the cervical vaginal secretion samples are then determined by an antibody sandwich ELISA. As an initial step, antibody against L-PGDS raised in rabbits is purified by hydroxyapatite chromatography, followed by an immunoaffinity purification on an Affi-Gel 15 Gel column.

The purified antibody is then diluted to 10 µg/ml in 0.2M sodium carbonate buffer, pH 9.0, and 50 µl added to each well of an Nunc-Immuno plate with Maxi Sorp surface overnight at 4° C. The wells are then washed with 0.1% BSA/0.05% Tween 20 in PBS 4 times and blocked with 1% BSA in PBS for 1 hour. Diluted plasmas or L-PGDS standards (1.2 to 75 ng/ml) are incubated in Block for 90 minutes, then washed as above. A secondary anti-L-PGDS antibody, raised in chickens, at 4 ng/ml in wash buffer, is incubated in the wells for 1 hour and then washed, as above. Horseradish peroxidase-tagged goat anti-chicken antibody at 1:10,000 in wash buffer is added for 1 hour and then the plate is washed, as above, developed in a 0.01 3,3', 5,5' tetramethylbenzidine solution, stopped with 50 µl of 1N sulfuric acid, and read at 450 nm in a microplate reader. L-PGDS concentration is determined by the standard curve obtained by plotting the absorbance versus the corresponding concentration of an L-PGDS standard.

This assay is also adapted to a BioPlex suspension array for similar quantitation. The assay is also amenable for development to run the samples on a 2-D PAGE and determine the particular L-PGDS isoforms present/absent from the CVS samples that may be indicative of an increased propensity toward preterm birth. It is understood and believed that an antibody to the specific isoform may be created to fine-tune the detection method.

In assessing test samples, L-PGDS concentrations determined by ELISA are normalized to protein levels in the CVS. Protein content of the samples is determined by BCA method, which has been commonly used to quantitate protein levels in cell lysates.

The new markers of the present invention are highly sensitive and specific (e.g., 90% or higher). In an preliminary study, at a level of 90% specificity, the sample size yields a 95% confidence level, indicating high precision, with a margin of error of about 5%. The collection of test data from pregnant women is ongoing and studies producing significant results have been established as demonstrated in the following Table 1.

TABLE 1

| CVS L-PGDS (ng/ml) | | | | | | | |
|---|---|---|---|---|---|---|---|
| Term | | | | Preterm | | | |
| Patient ID # | CVS (weeks) | Term Delivery | Days to Delivery | Patient ID # | CVS (weeks) | Preterm Delivery | Days to Delivery |
| 17 | 26 | 607 | 84 | 20 | 30 | 7653 | 11 |
| 19 | 26 | 725 | 86 | 21 | 30 | 4839 | 24 |
| 24 | 26 | 818 | 93 | 23 | 32 | 2589 | 2 |
| 26 | 31 | 1163 | 58 | 28 | 28 | 1033 | 2 |
| 27 | 33 | 282 | 32 | 30 | 32 | 4926 | 1 |
| 29 | 25 | 782 | 85 | MEAN | 30 | 4208 | 8 |
| 31 | 25 | 872 | | SEM | 1 | 761 | 3 |
| 33 | 30 | 1798 | 57 | | | | |
| 34 | 29 | 2717 | 66 | | | | |
| 36 | 25 | 1056 | | | | | |
| 37 | 27 | 1308 | | | | | |
| MEAN | 28 | 1103 | 70 | | | | |
| SEM | 1 | 201 | 6 | | | | |

Figure 1A:
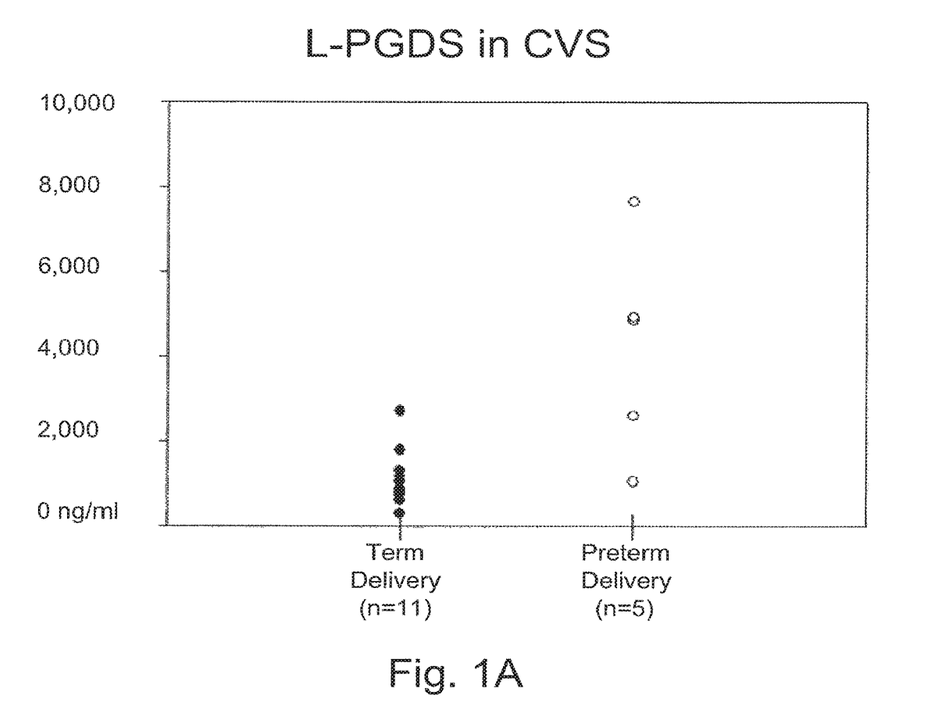
FIGS. 1A and 1B present data from a preliminary study of samples of pregnant women correlating L-PGDS levels in cervical vaginal secretions with term or preterm delivery.
Figure 1B:
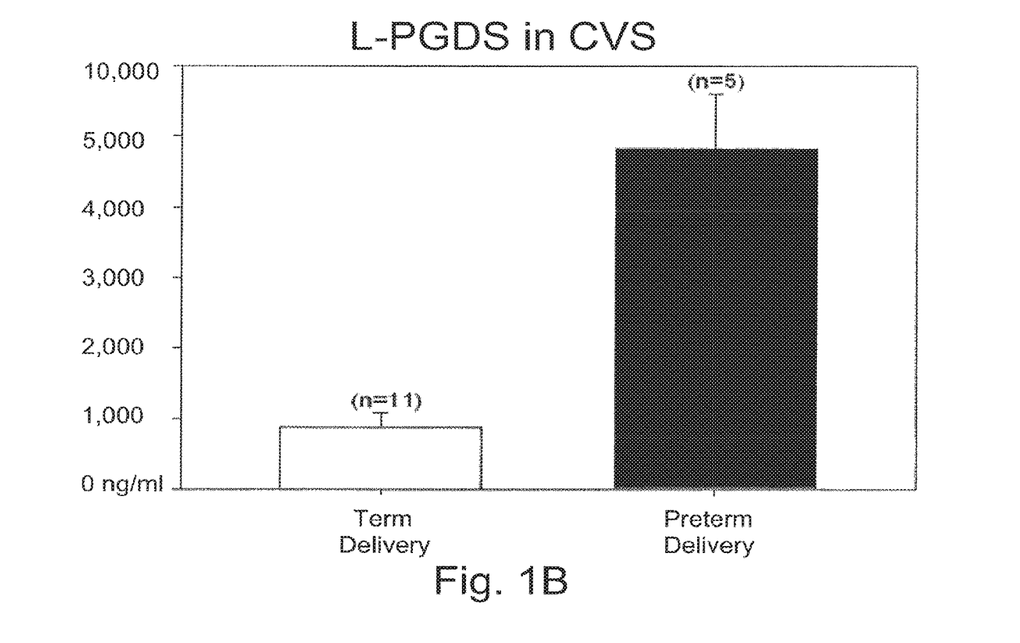

Notes:
Current samples collected at between 28-30 weeks of gestation
Level of L-PGDS ~4-fold higher than in pregnancies that go to term
Average time until delivery based on elevated L-PGDS 8 days vs. 70 days with lower levels
Currently a cutoff of <1.8 µg/ml L-PGDS would appear to distinguish ~91% of term deliveries Statistical analysis of this data indicates that high L-PGDS levels (i.e., L-PGDS levels above 1.8 µg/ml) predict an increased likelihood of preterm delivery in human subjects. Graphical illustration of this analysis is depicted in FIGS. 1A and 1B. Findings from the studies indicate that L-PGDS levels in pregnant women susceptible to preterm delivery average a 4-fold increase over levels in women whose pregnancies go to term, and that the average time until delivery for women with elevated L-PGDS levels is 8 days, compared to 70 days for those women that do not demonstrate such elevated levels.

The pattern of elevated L-PGDS in preterm is generally consistent with the predicted rise. Because the L-PGDS level has a normal change over gestation, CVS samples are preferably taken and L-PGDS assays performed every two weeks.

A key advantage of this assay over the current fetal fibronectin (fFN) test is that the present assay would predict preterm birth over the entire gestational period up to parturition. A negative fFN, although very accurate, is only valid for a 2-week window. Interestingly, in the study reported below, there were several samples that were fFN negative, but ultimately went preterm. The present assay showed elevated L-PGDS, and was predictive for preterm birth.

Figure 2:
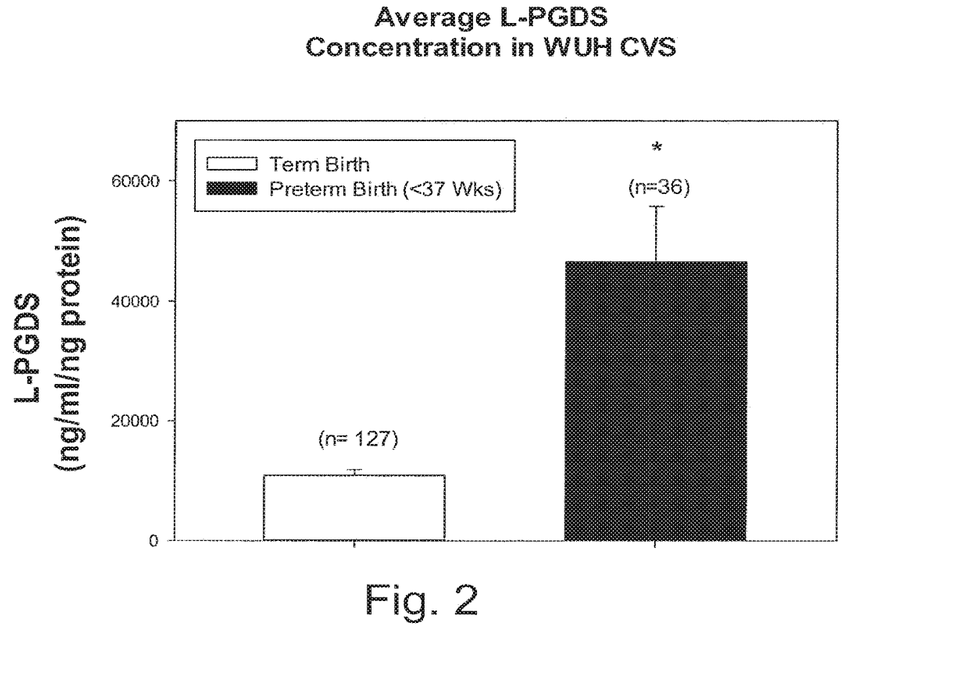
FIG. 2 present data from a study of samples of pregnant women correlating L-PGDS levels in cervical vaginal secretions with term or preterm delivery.

FIG. 2 shows results from a larger study. The data shows that for 163 patients, 36 were preterm (birth less than 37 weeks gestation), with a median of L-PGDS of 8,566 ng/ml/ng protein and 127 went to term with an median of 28,247 ng/ml/ng protein. Results showed that difference in the median values between the two groups is greater than would be expected by chance; there is a statistically significant difference (P=<0.001). See Table 2.

TABLE 2

Mann-Whitney Rank Sum Test

| Group | N | Missing | Median | 25% | 75% |
|---|---|---|---|---|---|
| Preterm | 36 | 0 | 28247.587 | 17051.503 | 47944.682 |
| Term | 127 | 0 | 8566.720 | 4663.511 | 12857.063 |

Mann-Whitney U Statistic = 694.000
T = 4544.000 n(small) = 36 n(big) = 127 (P = <0.001)

The difference in the median values between the two groups is greater than would be expected by chance; there is a statistically significant difference (P=<0.001)

Figure 3:
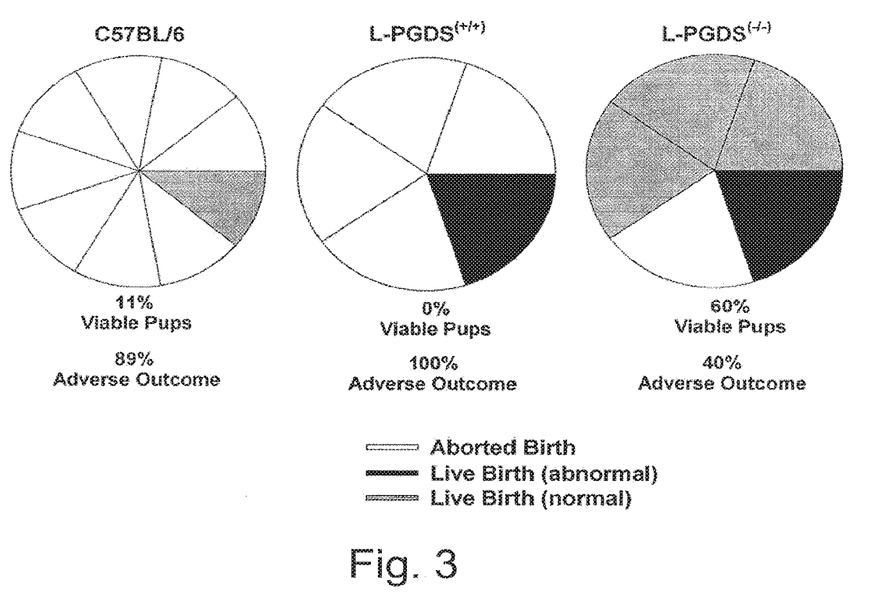
FIG. 3 presents data from (murine) animal studies to demonstrate the relationship between lower L-PGDS levels and likelihood of viability and successful term birth.

Animal studies conducted to determine the correlations between L-PGDS concentrations and birth viability and/or risk of preterm birth were conducted with L-PGDS knockout mice and transgenic L-PGDS overexpressor mice. Results are demonstrated in FIG. 3. The studies strongly validate the present findings that lower concentration levels of L-PGDS tend to increase the chances of successful term birth, as per the present murine model. The findings from these animal studies cross-validate the findings from human studies (e.g., as presented above in Table 1).

Table 3 shows data demonstrating that in LPS-induced preterm birth, there is a three-fold increase in viable mouse pups/pregnancy in the L-PGDS knockouts and a 15-fold decrease in viable pups/pregnancy in the L-PGDS transgenic overexpressors when compared to the C57BL/6 controls. This implies that L-PGDS is casually related to preterm birth, and not merely correlated with it.

mon elements, it is likely that the prostaglandin D2 receptor antagonists will also act to block preterm labor from other causes.

Chemical compounds which influence the levels of L-PGDS in pregnant women might be administered as tocolytic therapeutic agents. Preferred embodiments of such effective tocolytic agents include prostaglandin D2 (DP1 or DP2) receptor antagonists, such as BWA868C, see, e.g., U.S. Pat. Nos. 6,395,499; 6,878,522; 6,884,593; 7,144,913; 7,217,725; 7,517,889; 7,642,249; 8,067,445; 8,071,807; 8,193,183; 8,242,145; 8,338,484; 8,362,044; 8,378,107; 8,383,654; 8,426,449; 8,497,381; 8,501,959; 8,524,748; U.S. Pat Pub. Nos. 20020022218; 20030027854; 20040162323; 20040180934; 20040185509; 20040197834; 20050215609; 20070054951; 20070244131; 20070249686; 20070265278; 20070265291; 20080194600; 20080261922; 20090036469; 20090176804; 20090197959; 20100004331; 20100075990; 20100081673; 20100113503; 20100130574; 20100298368; 20110021573; 20110039852; 20110098302; 20110098352; 20110112134; 20110130453; 20110144160; 20110152338; 20110190227; 20110245303; 20110301168; 20110312974; 20110318308; 20110319445; 20120004233; 20120016029; 20120022119; 20120058123; 20120059055; 20130005728; 20130005741; 20130065902; 20130079375; 20130109685; 20130158036; each of which is expressly incorporated herein by reference. Methods of treatment and preventing preterm delivery include the administration of a therapeutic amount of prostaglandin D2 receptor antagonists to a pregnant woman in need thereof. Proper routes of administration, dosages and frequencies of administration of these tocolytic agent prostaglandin D2 receptor antagonists may be readily determined by one of skill in the art, e.g., medical practitioners.

More particularly, the present invention provides for methods of treating preterm labor via the administration of pharmaceutical compositions comprising active tocolytic

TABLE 3

| Experiment # | C57BL/6 | | | | | | | L-PGDS KO | | | | | | | L-PGDS KI | | | | | | |
|---|---|---|---|---|---|---|---|---|---|---|---|---|---|---|---|---|---|---|---|---|---|
| | 1 | 2 | 3 | 4 | 5 | Total | SEM | 1 | 2 | 3 | 4 | 5 | Total | SEM | 1 | 2 | 3 | 4 | 5 | Total | SEM |
| Pregnant Females | 2 | 4 | 3 | 5 | 3 | 17 | 0.5 | 0 | 3 | 2 | 3 | 2 | 10 | 0.5 | 0 | 1 | 4 | 4 | 6 | 15 | 1.1 |
| Viable Pups | 1 | 5 | 0 | 5 | 7 | 18 | 1.3 | 0 | 8 | 9 | 16 | 0 | 33 | 3.0 | 0 | 0 | 0 | 1 | 0 | 1 | 0.2 |
| Adverse Outcome | 15 | 19 | 21 | 12 | 10 | 77 | 2.1 | 0 | 2 | 1 | 11 | 2 | 16 | 2.0 | 0 | 4 | 23 | 25 | 56 | 108 | 9.9 |
| Viable Pups/Pregnancy | | | | | | 1.06 | | | | | | | 3.30 | | | | | | | 0.07 | |

In a study of pregnant C57BL/6 mice implanted with Alzet osmotic pumps containing both DP1 and DP2 antagonists (BWA868C and 11-deoxy-11-methylene prostaglandin D2 at 1.0 μg/μl or PBS vehicle) were injected with lipopolysaccharide (LPS) (20 μg) at day 14 of pregnancy to induce preterm birth. In the LPS-only control group, 80% suffered adverse outcomes (premature birth or fetal death), and 20% had normal outcomes. In the experimental group, LPS plus DP1 and DP2 antagonist, 50% suffered adverse outcomes and 50% had normal outcomes. This demonstrates that administration of prostaglandin D2 receptor antagonists may be administered to pregnant mammals to interrupt preterm labor, and more particularly, to avoid preterm labor induced by infectious agents, especially those which produce lipopolysaccharides. Because the preterm labor pathway has comtherapeutic agents with a pharmaceutically acceptable carrier. Pharmaceutical composition of the present invention are intended to encompass a product comprising the active ingredient(s), e.g., prostaglandin D2 receptor antagonists, and the inert ingredient(s) (pharmaceutically acceptable excipients) that constitute the carrier, as well as any product which may result, directly or indirectly, from combination, complex formation or aggregation of any two or more of the ingredients, or from dissociation of one or more of the ingredients, or form other types of reactions or interactions of one or more of the ingredients.

For example, available prostaglandin D2 (DP1/DPGTR, DP2/CRTH2) receptor antagonists include AM156 ({2'-[(cyclopropanecarbonyl-ethyl-amino)-methyl]-6-methoxy-4'-trifluoro-methyl-biphenyl-3-yl}-acetic acid, sodium salt), and AM206 (5-{2-[(benzoyloxycarbonyl-ethyl-amino)-methyl]-4-trifluoromethyl-phenyl}-pyridin-3-yl)-acetic acid, sodium salt), MK-0524 ([(3R)-4-(4-Chloro-benzyl)-7-fluoro-5-(methylsulfonyl)-1,2,3,4-tetrahydrocyclopenta[b]indol-3-yl]acetic Acid), AM-853 (2-(4-(4-(tert-butylcarbamoyl)-2-(2-chloro-4-cyclopropylphenyl sulfonamido)phenoxy)-5-chloro-2-fluorophenyl)acetic acid), BW868C (3-benzyl-5-(6-carbohexyl)-1-(2-cyclohexyl-2-hydroxyethylamino)-hydantoin), S-5751 ((Z)-7-[(1R,2R,3S,5S)-2-(5-hydroxy benzo[b]thiophen-3-ylcarbonylamino)-10-norpinan-3-yl]hept-5-enoic acid), BAY-u3405 (Ramatroban, 3(R)-[[(4-fluorophenyl) sulphonyl]amino]-1,2,3,4-tetrahydro-9H-carbazole-9-propanoic acid). Such agents, or others that are known or become known, may be used alone, in combination or subcombination. In some cases, the effects may be enhanced by selectively acting on DP1 or DP2, and therefore appropriate agents may be selected. Likewise, as may be appropriate, a mixed agonist/antagonist comprising a single or multiple agents, may be administered or concurrently administered.

For the treatment of preterm labor, the tocolytic therapeutic agents may be administered orally, by inhalation spray, topically, transdermally, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Tocolytic therapeutic agents, e.g., prostaglandin D2 receptor antagonists, may be co-administered with other therapeutic agents and are suitable for simultaneous and/or sequential combination therapies. Methods of the present invention further encompass co-administration to a pregnant woman of a non-toxic therapeutically effective amount of a tocolytic therapeutic agent, such as a prostaglandin D2 receptor antagonist, optionally with other active therapeutic agents, e.g., other prostaglandin D2 receptor antagonists, either simultaneously or sequentially as part of a combination therapy treatment regimen. Similarly, a selective L-PGDS inhibitor, such as AT-56 (4-dibenzo[a,d]cyclohepten-5-ylidene-1-[4-(2H-tetrazol-5-yl)-butyl]-piperidine) may be used alone or in combination with a DP1 and/or a DP2 antagonist. The therapeutic amounts of active therapeutic agents as administered in combination therapy may be those as commonly used for each active therapeutic agent when administered alone, or the amounts may result in lower dosage(s) for one or more of the active therapeutic agents.

Figure 4:
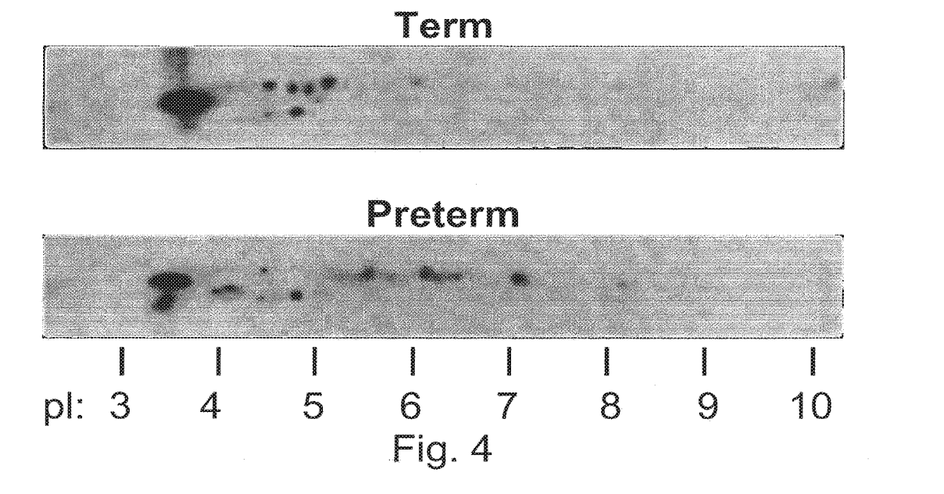
FIG. 4 shows 2D PAGE of Human CVS L-PGDS Isoforms.

As shown in FIG. 4, different isoforms of L-PGDS appear in preterm birth CVS samples than for at term births. Therefore, a selective immunoassay may be implemented based on the ability of certain antibodies to distinguish between the isoforms. Immunoassays may include radio immunoassays, enzyme-linked immunoassays, fluorescent immunoassays, and the like.

On the other hand in a ratiometric assay which seeks to determine a ratio between isoforms, or between a single isoform and the total, during purification, it may be preferred to avoid selective enrichment, and thus immunopurification may employ a non-specific antibody or a balanced mix of antibodies to ensure that the CVS sample concentrations are not altered during processing. Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method for predicting preterm delivery of a fetus, comprising:
   collecting a cervical vaginal secretion sample from a pregnant woman having an intact amniotic membrane;
   measuring with an immunoassay lipocalin-type prostaglandin D2 synthase (L-PGDS) concentration in the collected cervical vaginal secretion sample; and
   determining a likelihood of preterm delivery based on a comparison of the measured lipocalin-type prostaglandin D2 synthase concentration to corresponding values from a gestational age-matched population.

2. The method of claim 1, wherein the L-PGDS concentration in the cervical vaginal secretion rises prior to rupture in membranes.

3. The method of claim 1, wherein measuring lipocalin-type prostaglandin D2 synthase concentration comprises measuring ratios of isoforms of L-PGDS in the collected cervical vaginal secretion sample.

4. The method of claim 1, wherein the cervical vaginal secretion is collected with a sponge.

5. The method of claim 4, wherein the sponge is treated with at least a protease inhibitor and a bacteriocide.

6. The method of claim 1, wherein L-PGDS levels of above 1.8 µg/ml indicate the increased likelihood of preterm delivery.

7. The method of claim 1, wherein the likelihood of preterm delivery is the likelihood of preterm delivery within a period greater than 2 weeks.

8. The method of claim 1, wherein the pregnant woman is at week 28 of gestation or later.

9. The method of claim 1, further comprising repeating cervical vaginal secretion collection from the pregnant woman and L-PGDS measurement every two weeks.

10. The method of claim 1, further comprising delaying the preterm delivery by administering to the pregnant woman a composition comprising a tocolytic agent.

11. The method of claim 10, wherein the tocolytic agent is a β2 agonist, an NSAID cyclooxygenase inhibitor, a calcium channel blocker, a prostaglandin DP1 or DP2 receptor antagonist, or an oxytocin inhibitor.

12. The method of claim 1, wherein the L-PGDS concentration is measured using a radioimmunoassay, enzyme-linked immunoassay, or fluorescent immunoassay.

13. The method of claim 1, wherein measuring L-PGDS comprises contacting the cervical vaginal secretion sample with at least one antibody against L-PGDS.

14. The method of claim 2, wherein measuring L-PGDS concentration comprises contacting the cervical vaginal secretion sample with multiple antibodies against isoforms of L-PGDS.

15. The method of claim 1, wherein the cervical vaginal secretion sample is collected at or after 25 weeks gestation.

* * * * *